United States Patent [19]

Thorpe

[11] 4,053,528

[45] Oct. 11, 1977

[54] PROCESS FOR THE PREPARATION OF DIELS-ALDER ADDUCTS OF HALOGENATED CYCLOPENTADIENES

[75] Inventor: Donald H. Thorpe, Williamsville, N.Y.

[73] Assignee: Hooker Chemicals & Plastics Corporation, Niagara Falls, N.Y.

[21] Appl. No.: 566,487

[22] Filed: Apr. 9, 1975

Related U.S. Application Data

[63] Continuation-in-part of Ser. No. 429,454, Dec. 28, 1973, abandoned.

[51] Int. Cl.$^2$ .............................................. C07C 17/00
[52] U.S. Cl. ............................ 260/648 C; 260/648 R; 260/611 R; 260/611 A
[58] Field of Search ........... 260/648 C, 648 R, 611 R, 260/611 A

[56] References Cited

U.S. PATENT DOCUMENTS

| | | | |
|---|---|---|---|
| 2,217,632 | 10/1940 | Wolfe | 260/464 |
| 3,050,567 | 8/1962 | Schmerling | 260/648 C |
| 3,205,274 | 9/1965 | Mark | 260/648 C |
| 3,221,066 | 11/1965 | Hoch | 260/648 C |
| 3,396,201 | 8/1968 | Weil et al. | 260/648 C |

OTHER PUBLICATIONS

Migrdichian, Organic Synthesis, vol. 2, 1062–1063 (1957).

Primary Examiner—C. Davis
Attorney, Agent, or Firm—P. F. Casella; W. J. Crosetta; D. A. Stein

[57] ABSTRACT

An improved process for the preparation of solid Diels-Alder adducts of halogenated cyclopentadienes and mono- or diolefins is disclosed wherein the reactants are combined in an aqueous emulsion. The adducts are obtained in excellent yield and in an extremely fine particulate form. The new process avoids the use of organic solvents which are relatively costly, hazardous to use, and from which the adducts are usually obtained as relatively large crystals which require pulverization prior to use.

16 Claims, No Drawings

PROCESS FOR THE PREPARATION OF DIELS-ALDER ADDUCTS OF HALOGENATED CYCLOPENTADIENES

CROSS REFERENCE TO RELATED APPLICATION

This application is a continuation-in-part application of U.S. application Ser. No. 429,454 filed Dec. 28, 1973 now abandoned.

FIELD OF THE INVENTION

This invention relates to an improved process for the preparation of Diels-Alder adducts. More particularly, it relates to improvements in the preparation of solid adducts of halogenated cyclopentadienes and mono- or diolefins.

BACKGROUND OF THE INVENTION AND RELATION TO THE PRIOR ART

The Diels-Alder adducts of non-polymeric mono- and diolefins with halocyclopentadienes, particularly cyclopentadienes wherein the carbon atoms of the conjugated double bonds are completely substituted with halogen, i.e. perhalogenated, are known and have become commercially important as fire retardant additives for various polymers (see e.g., U.S. Pat. No. 3,403,036) and as insecticides (See U.S. Pat. No. 2,635,977, U.S. Pat. No. 3,356,688).

The preparation of such solid adducts has been carried out either by direct combination, i.e. by reaction in bulk, of the reactants at atmospheric pressure or superatmospheric pressure (see e.g. U.S. Pat. No. 3,050,567) or by heating an organic solvent solution of the reactants (see e.g. col. 3, lines 46–47 of the aforementioned U.S. Pat. No. 3,050,567).

In the first of these prior art procedures the adduct is usually obtained in low yield and in a crude form which requires tedious and costly purification procedures. Moreover the product is often solidified with difficulty and when recovered form is in the form of a massive crystalline body or aggregate which is difficult to break up into finely divided particles using conventional techniques such as trituration or heating with an organic solvent.

In the second procedure the use of organic solvents is expensive due to the necessity of recovering them and they are hazardous to personnel and equipment. In many instances, the adducts also solidify from the solvent solution as relatively large crystals which require pulverization prior to use as fire retardant additives since it is generally known that to be most effective in this application and to have the least effect on the physical properties of the polymer composition, the particle size of the additive should be as small as possible.

It is known to carry out the Diels-Alder reaction of open chain dienes e.g. 1,3-butadiene and beta chloro-1,3-butadiene, with olefinic and diolefinic dienophiles in aqueous emulsion or suspension as disclosed in U.S. Pat. No. 2,217,632; 2,222,357 and 2,262,002 but none of these references suggest use of an emulsion reaction technique to provide a finely divided particulate product. Many such Diels-Alder reactions of open chain dienes are distinguished from the corresponding Diels-Alder reactions of halocyclopentadienes in producing a liquid rather than a solid adduct, i.e, an adduct which is a solid at ambient temperature. Moreover the Diels-Alder adduction of such open chain dienes is distinguished from the diels-Alder adduction of the halocyclopentadienes on the basis of the known extensive difference in the Diels-Alder reactivity between such open chain dienes and cylic dienes such as the halocyclopentadienes. The sensitivity of the Diels-Alder reaction to such steric factors is more particularly discussed in A. Wasserman, "Diels-Alder Reactions", Elsevier Publishing Company, 1965, see especially Chapter 5.

It is also known to carry out in aqueous suspension the Diels-Alder reaction of an oleginic dienophile, e.g. maleic anhydride, with furan, a heterocyclic diene, as disclosed in O. Diels et al. Ann. 490 243 (1931), see especially p. 247. The reference reaction undesirably provides an adduct in the form of large flakes (see p. 247, seventh line from the bottom of the page of O. Diels et al. op. cit.). Moreover, the adduction reaction of the O. Diels et al. reference is distinguished from those of halocyclopentadienes in employing a heterocyclic diene reactant i.e. furan, rather than a homocyclic diene reactant as in the Diels-Alder reactions of the halocyclopentadienes.

It is further known to carry out in aqueous emulsion the Diels-Alder reaction of non-polymeric mono- and diolefinic dienophiles with cyclopentadiene devoid of halogen substituents as is disclosed in aforementioned U.S. Pat. No. 2,262,002. However the Diels-Alder reactions of non-halogenated cyclopentadiene are distinguished from those of the halocyclopentadienes by the known large difference in Diels-Alder reactivity between non-halogenated dienes and the corresponding halogenated dienes as indicated, for example, by a comparison of the Diels-Alder reaction rates of butadiene and chloro butadiene and of cyclopentadiene and hexachlorocyclopentadiene with the same dienophile as disclosed in S. Patai, editor, "The Chemistry of Alkenes" Interscience Publishers 1964, p. 921, Table 22.

U.S. Pat. No. 3,444,154 discloses the condensation of halocyclopentadienes and polymerized diolefins in aqueous emulsion. The reference, which also does not disclose the use of the emulsion reaction technique to achieve small product particle sizes, relates to a reaction wherein the dienophile reactant and the product are invariably polymeric substances and hence, distinguished from the Diels-Alder reactions of halocyclopentadienes with nonpolymeric mono- and diolefinic dienophiles wherein the reactants and products ae non-polymeric substances and the dienophiles contain at most, two olefinic carbon to carbon double bonds per molecule. The reaction of the reference is further distinguished from the Diels-Alder reaction of halocyclopentadienes with non-polymeric mono- and diolefinic dienophiles in not proceeding to substantially complete adduction of the unsaturation in the polymeric reactant, i.e. even under the most drastic reaction conditions and/or in the presence of stoichiometric excesses of the diene no more than about 49–83% of the ethylenic unsaturation in the diolefin polymer is adducted. (See for example, Example 4 of U.S. Pat. No. 3,444,154 wherein use of about a two hundred mole percent excess of hexachlorocyclopentadiene produces only about 82.9% adduction).

OBJECTS OF THE INVENTION

It is thus a principal object of the present invention to devise an improved process for the preparation of slid Diels-Alder adducts.

Another object is to devise a process for the preparation of Diels-Alder adducts in high yields and in fine particulate form.

A specific object is to devise an improved process for the preparation of the solid adducts of halogenated cyclopentadienes and mono or diolefins which includes the step of carrying out the adduction in the presence of an aqueous emulsion of the reactants.

Other objects of the invention will be apparent from the following detailed description.

BRIEF SUMMARY OF THE INVENTION

In accordance with the present invention halogenated cyclopentadienes and mono or diolefins are suspended in aqueous media and caused to react therein to form Diels-Alder adducts.

Preferably the halocyclopentadienes employed as diene reactants in the improved Diels-Alder adduction process of the invention are polyhalogenated cyclopentadienes wherein at least all the carbon atoms of the diene system, i.e. of the conjugated carbon to carbon double bonds, are perhalogenated.

Preferably the reaction is effected in the presence of an organic surfactant. The reaction may be carried out at temperatures ranging from ambient temperature to the boiling point of the aqueous medium or at still higher temperatures with the use of super atmospheric pressures. In general the particular conditions of reaction temperature, pressure and reactant proportions employed in the present improved process will be substantially similar to those employed in corresponding prior art Diels-Alder reactions of halocyclopentadiene which do not employ the present novel emulsion reaction technique i.e. bulk or solvent techniques for carrying out the adduction of the halocyclopentadienes with mono- and diolefinic dienophiles.

DETAILED DESCRIPTION OF THE INVENTION

In accordance with a preferred mode of carrying out the process of the invention a mono-olefin or diolefin and at least a molar equivalent proportion of a halogenated cyclopentadiene of the formula

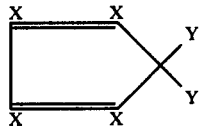

wherein X is a halogen selected from the group consisting of fluorine, chlorine, and bromine, and Y is independently selected from the group consisting of fluorine, chlorine, bromine, alkyl of 1 to 10 carbon atoms, preferably 1 to 6 carbon atoms, alkoxy of 1 to 10 carbon atoms, preferably 1 to 6 carbon atoms, haloalkyl of 1 to 10 carbon atoms, preferably 1 to 6 carbon atoms, and haloalkoxy of 1 to 1 carbon atoms, preferably 1 to 6 carbon atoms, wherein the halogen is fluorine, chlorine or bromine, is suspended in an aqueous media, preferably containing an organic surfactant, and caused to react therein, and thereafter separating the adduct product in finely divided particulate form having substantially no particles with a maximum size greater than about 200 microns.

In the reaction of halogenated cyclopentadienes with mono-olefins, preferably about one molar proportion of the halogenated cyclopentadiene is reacted with one molar proportion of the mono-olefin, but slight excess proportions up to about 10 mole percent of either reactant can be employed.

In the reaction of halogenated cyclopentadienes with diolefins to produce diadducts, preferably about two molar proportions are reacted with one molar proportion of the diolefin, but slightly excess proportions up to about 1 mole percent of either reactant can be employed. When monoadducts of the diolefins are prepared, the proportions of reactants are the same as for mono-olefins.

Representative examples of the halogenated cyclopentadienes which are suitable for use in this invention, include the following:

hexafluorocyclopentadiene
hexachlorocyclopentadiene
hexabromocyclopentadiene
5,5-difluorotetrachloro-cyclopentadiene
tetrabromodichlorocyclopentadiene
5,5-dimethoxy tetrachlorocyclopentadiene
5,5-dibromotetrachlorocyclopentadiene
5-butyl pentachlorocyclopentadiene
tetrafluorodibromocyclopentadiene
5pentachlorocyclopentadiene
5-methyl, 5-octyl-tetrachloropentadiene
5,5-dibutyl-tetrafluorocyclopentadiene
5-decyl-pentabromocyclopentadiene
5,5-dihexyl-tetrachlorocyclopentadiene
5,5-dinonyl-tetrafluorocyclopentadiene
5-methoxy-pentachlorocyclopentadiene
5-amyloxy-pentabromocyclopentadiene
5-decyloxy-1-pentoxy-tetrafluorocyclopentadiene
5-methoxy-5-ethoxy-tetrabromocyclopentadiene
5-propxoy-5-hexoxy-tetrachlorocyclopentadiene
5,5-diethoxy-tetraflurorocyclopentadiene
5-methoxy-5-nonoxy-tetrachlorocyclopentadiene
5-chloromethyl-pentachlorocyclopentadiene
5,(3'-bromopropyl)-pentabromocyclopentadiene
5-(fluorooctyl)-pentafluorocyclopentadiene
5,5-bis(chloromethyl)-tetrachlorocyclopentadiene
5,5-bis(bromohexyl)-tetrafluorocyclopentadiene
5,5-bis(fluorodecyl)-tetrabromocyclopentadiene
5-ethyl-5-chloromethyl-tetrachlorocyclopentadiene
5(2'-chloroethyl)pentachlorocyclopentadiene Mixtures of these and equivalent halocyclopentadienes can also be employed as the diene reactant in the present improved Diels-Alder reaction process.

The preferred halogenated cyclopentadiene is hexachlorocyclopentadiene because of its relatively low cost and general availability. Hereinafter primary reference will be made to hexachlorocyclopentadiene, however any halogenated or halocyclopentadiene as defined above may likewise be employed The monoolefin compounds for use as dienophiles in preparing Diels-Alder adducts with the halogenated cyclopentadienes include open chain and cyclic aliphatic olefins, including aryl alkenes, of 5 to 10 carbon atoms, which in addition to hydrogen may be substituted with carboxylic acid groups including lower alkyl (i.e. alkyl of 1 to 10 carbon atoms) carboxy groups (i.e. ester) and carboxylic anhydride groups; keto groups; aldehyde groups; nitrile groups; halogen, hydroxyl and other such conventional substituents. Typical suitable mono-olefin dienophiles for use in the invention are illustrated by, but are not limited to, the following examples.

Cyclopentene
Cyclohexane
Cycloheptene
Cyclooctene
1-methylcyclopentene
methyl vinyl ketone
allyl chloride
diisopropyl maleate
n-decylacrylate
norbornene
4-propyl-cyclohexene
5-sec-butylcyclohexane
1-methyl-4-isopropyl cyclohexane
3,3,6,6-tetramethylcyclohexene
Styrene
Vinyl toluene
Maleic anhydride
Allyl alcohol
Methyl acrylate
Ethyl acrylate
Methyl methacrylate
Acrylonitrile Mixtures of these and equivalent or homologous mono-olefins may also be employed as the dienophile reactant in the improved process of the invention.

Typical diolefin compounds suitable for use as dienophiles in preparing Diels-Alder adducts with the halogenated cyclopentadiene according to the invention include aliphatic, cycloaliphatic and aromatic hydrocarbons of 5 to 12 carbon atoms, which are illustrated by, but not limited to, the following representative examples:
Furan
Cyclopentadiene
Dicyclopentadiene
Cyclohexadiene
Methyl cyclopentadiene
Bicyclo(2,2,1)heptadiene 1,5-cyclooctadiene
Cyclodecadiene
Cyclodedecadiene
1,3-butadiene
Methyl butadiene
1,5-hexadiene
1,7-octadiene
1,3-octadiene
1,5-octadiene
1,11-dodecadiene
Divinyl benzene
Limonene
Vinyl norbornene
Ethylidene norbornene
Vinyl cyclohexane Mixtures of these and equivalent or homologous diolefins may also be employed as the dienophile reactant in the improved process of the invention.

Mono- and diolefins for use as dienophiles in the invention are desirably devoid of substitutents conjugated with the dienophile unsaturation which are known to activate the dienophile toward condensation in the Diels-Alder activating substituents are electron withdrawing groups such as carboxylic acid substituents (including acid anhydride and ester substituents), nitrile groups, keto groups, and aldehyde groups In carrying out the process of this invention an aqueous emulsion of the halogenated cyclopentadiene containing about a molar equivalent amount of the mono- or diolefin is initially prepared and caused to react to form the adduct product. Emulsions are a substantially permanent heterogeneous liquid mixture of two or more liquids or liquids and solids which are not normally mutually soluble in each other but are held in suspension, one in the other, by mechanical agitation or by small amounts of additional substances known as emulsifiers or emulsifying agents. Preferably in this invention the emulsification of the reactants is assisted by the presence of an emulsifying agent and also, if desired, by mechanical agitation. However, either one or both emulsification aids may be used within the scope of this invention. Emulsification by mechanical agitation may generally be obtained through the use of conventional emulsifying equipment/ The emulsifiers which may be employed are a well known class or organic surface active agents. Such agents may be of anionic, cationic or nonionic class or may contain both anionic and cationic groups. The structural types of organic compounds useful as emulsifiers include higher alkyl (i.e alky of 1 to 25 carbon atoms) ammonium halides, sulfonated hydrocarbon oils, sodium or other alkali metal salts or organic phosphates, complex organic phoshates in free acid form, polyhydric alcohol esters and ethers, fatty acid soaps, mahogany soaps, i.e. the sodium salts and similar alkali metal salts of sulfonic acids of petroleum refining sludge, sorbitan fatty acid esters and other fatty acid esters, and aryl alkyl sulfonates, e.g. sodium or other water-soluble salts of benzene or naphthalene sulfonates substituted with higher alkyl groups which may be branched or straight chain alkyl groups. The foregoing enumeration is only a partial tabulation of cationic, anionic, and nonionic structural types of useful emulsifying agents which are more particularly described and identified with respect to structure in McCutcheons's *Detergentsand Emulsifiers* 1974 *Annual,* North American Edition, McCutcheon Divison of Allured Publishing Corp. Ridgeway, N. J., the pertinent disclosure of which is incorporated herein by reference. Conveniently, because of their ready availability, anionic surface active agents are employed as emulsification agents in the present process.

Further exemplifying organic emulsification agents which may be employed in the practice of the invention, is the following list of representative, typical commercial surfactants.

| Commercial Names | Chemical Names |
| --- | --- |
| Aerosol OT | Sodium octyl sulfo succinate |
| Aerosol GPG | A technical grade of Aerosol OT |
| Nekal WS 25 | Sodium sulfonate aliphatic polyester |
| Tamol SN | Sodium salt of the condensation product of formaldehyde and naphthalene sulfonic acid |
| Culverol DLS | Diethanolamine salt of lauryl sulfuric acid |
| Maprofix MSP90 | Sodium myristyl sulfate |
| Maprofix OX | Myristyl polyethoxy sodium sulfate |
| Gafac RM 510 ) | Free acid form of complex |
| Gafac RE 610 ) | organic phosphates |
| Gafac LO 529 | Sodium salt of complex organic phosphates |
| Arquad 2C 75 | Dicocomethyl ammonium chloride |
| Igepal LO-430 | Linear alkyl phenoxy poly (ethyleneoxy) ethanols |
| Triton X-35 | Octyl phenoxy poly(ethyleneoxy) ethanol |
| Brij 30 | Lauryl (polyethyleneoxy) ethanol |
| Sysonic E-30 | Tallow (polyethyleneoxy) ethanol |
| Aldo MR | Monoricinoleate ester of glycerine |

| Commercial Names | Chemical Names |
| --- | --- |
| Myrj 45 | Polyoxyethylene ester of stearic acid |
| Span 40 | Monopalmitate ester of sorbitan |
| Tween 65 | Polyoxyethylate derivtive of tristearate ester of sorbitan |
| Amidox C2 | Polyoxyethylene derivatives of cocoanut oil fatty acid amides |

Mixture of these and equivalent surfactants may be used also. It is often desirable to use such a mixture of emulsifiers so that a desired hydrophile-lipophile balance is achieved thereby insuring a more stable emulsion. The amount of emulsifier charged in the practice of the improved process of the invention is generally quite small in accord with conventional techniques for preparing aqueous emulsions of substantially water insoluble organic compounds. Usually the emulsification agent is employed in a concentration of from about 1% to about 5% based on the total weight of the halocyclopentadiene and olefin reactants although higher and lower amounts e.g. 0.1 to 10% by weight, can be used also.

Similar small concentrations of emulsion stabilizers such as polyvinyl-alcohol, methyl cellulose, hydroxy ethyl cellulose, hydroxy propyl cellulose, polyvinyl pryolidone and the like may be included in the aqueous emulsion also in accord with conventional techniques for preparing aqueous emulsions of substantially water-insoluble organic compounds.

In addition to the foregoing adjuvants, similar small proportions of buffers or alkaline agents such as disodium phosphate, sodium bicarbonate, sodium citrate, sodium hydroxide and the like may be added to the aqueous emulsion also and when present serve to neutralize any acidic materials present in the halogenated cyclopentadiene or formed during the adduction reaction. Epoxides such as epichlorohydrin and epoxidized soya oil can also be used as acid scavengers The temperature employed for this adduction reaction may be from about ambient (about 20° Centigrade) to about the boiling point of the aqueous emulsion when the reaction is carried out at a atmospheric pressure. Higher temperatures, up to the decomposition temperature of the reactants can be obtained when superatmospheric pressures and a suitable autoclave are employed. Satisfactory yields are generally obtained under normal atmospheric pressure conditions. However faster reaction can be sometimes obtained by conducting the reaction under superatmospheric pressure conditions. Thus the pressure employed in this reaction may range from atmospheric to about 100 atmospheres or higher, preferably from atmospheric to about 20 atmospheres and especially from atmospheric to about five atmospheres.

The reaction is conveniently completed in the majority of cases in from about 25 to about 48 hours depending upon the temperature and pressure. Higher temperatures and/or pressures favor faster reaction, i.e. completion of reaction in about 10 to 24 hours as will be obvious to those skilled in the art.

The emulsions prepared in accordance with the invention generally contain about 10 to about 60 weight percent of the halogenated cyclopentadiene and olefin reactants based on the total weight of the emulsion.

On completion of the Diels-Alder reaction according to the invention, the aqueous emulsion in the reaction mixture is broken, i.e, the organic and aqueous phases of the emulsion are caused to stratify into separate macroscopic layers, by conventional means such as the demulsification techniques described in S. Glasstone, "Textbook of Physical Chemistry," D. Van Nostrand Inc., Second Edition, 1946, p. 1277-1278, the pertinent disclosure of which is incorporated herein by reference. Particularly suitable means for breaking the emulsions in the present reaction mixtures include discontinuing mechanical agitation of the reaction mass and/or adding to the reaction mixture a small amount of a conventional demulsification agent, e.g. about 5 to 10%, based on the weight of the weight of the reaction mixture, of a completely water-miscible lower alkanol, such as methanol, or a completely water-miscible lower aliphatic ketone such as acetone. The resultant organic phase and aqueous phase are then separated by conventional techniques, e.g. filtration or decantation, to recover the product adduct.

The present improved process for carrying out the Diels-Alder adduction of haloclopentadienes is especially advantageous for preparing those halocyclopentadiene mono- and diadducts which are relatively high melting, i.e, which melt above about 160° C. While temperatures above 160° C. can be used in carrying out Diels-Alder adduction, such extreme reaction temperatures may and usually do effect at least some decomposition of the reactants or products. Accordingly unless a costly, hazardous organic solvent is employed, Diels-Alder preparation of such high melting adducts is not feasible since at reaction temperatures below about 160° C, the formation of the solid high melting adduct in the reaction generally results in a solidified reaction mass which cannot be agitated or stirred. Use of the aqueous emulsion technique of this invention avoids the necessity of employing costly, hazardous solvents or reactant or product-degrading reaction temperatures above 160° C in the preparation of the high melting adducts since the emulsified reaction mixture of the invention remains fluid and stirrable at reaction temperatures as low as ambient temperature. Typical high melting halocyclopentadiene adducts which can be prepared by the technique of the invention with the benefit of the aforementioned advantage include the diadduct of hexachlorocyclopentadiene and furan (m.p. 285°-286° C), the diadduct of hexachlorocyclopentadiene and cyclopentadiene (m.p. 170°-180° C), the diadduct of hexachlorocyclopentadiene and dicyclopentadiene (m.p. 255°-256° C.), the diadduct of hexachlorocyclopentadiene and 1,5-cyclooctadiene (m.p. above 300° C) and the mono adduct of hexachlorocyclopentadiene and cyclopentene (m.p. 165°-170° C).

Diels-Alder adduction of halocyclopentadienes employing the present aqueous emulsion technique also overcomes several additional serious disadvantages encountered when carrying out the corresponding adduction in bulk, i.e. in absence of an organic solvent or diluent. Thus solid product adduct is immediately obtained on breaking the emulsion in the reaction mixtures of the invention whereas the corresponding bulk process often yields oils or viscous liquids which may require long term standing before solidification occurs. Secondly the present process affords the product adduct in finely divided particulate form whereas the bulk process provides adduct in the form of one or several massive crystalline aggregates or bodies which are difficult to remove from the reaction vessel without tedious, costly trituration and/or heating with organic solvents in an additional recovery step. Even when the product of the bulk process is treated in such an additional step to recover it in particular form, the maximum size of particles therein is substantially larger than that of the corresponding product obtained in accordance with the emulsion technique of the invention (see Example 14 below).

The Diels-Alder reaction of the invention provides an excellent recovery of product adduct. In other words according to the invention on adduct recovery of above about 80% or greater of theory is generally achieved on completion of the present adduction even when no stoichiometric excess of the halocyclopentadiene is employed. In the presence of the above described stoichiometric excess of the diene, the yield of adduct is generally substantially quantitative i.e. of the order of above about 90% to about 100% of theory.

The following examples illustrate the process of this invention In these examples, as well as in the above description and following claims, parts and percentages are by weight and temperatures are given in degrees Centigrade unless otherwise specified.

RE 610, 67.2 parts of trisodium phosphate ($Na_3PO_4.12H_2O$) and 3000 parts of distilled water was heated in autoclave equipped with an agitator for about 24 hours at 110 degrees. The maximum pressure developed was about eight pounds per square inch gauge. After cooling to ambient temperature the reaction mixture was removed from the autoclave, the emulsion was broken by the addition of acetone, and the precipitated product was separated by filtration. The filter cake was washed with acetone and then dried. The yield of diadduct obtained amounted to 91.2 percent of the theoretical amount and the product had a maximum particle size of 40 microns.

EXAMPLES 3-12

The procedure described in Example 1 above was repeated utilizing various emulsifying agents and various proportions of reactants and other components of the reaction mixture. The formulations and results obtained are set out in the following table.

TABLE

| | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|
| 1,5-Cyclooctadiene | 10.8 | 21.6 | 21.6 | 21.6 | 21.6 | 21.6 | 21.6 | 21.6 | 27 | 51 |
| Hexachlorocyclopentadiene | 57.0 | 114 | 119.2 | 114 | 114 | 114 | 114 | 114 | 141 | 273 |
| Polyvinyl Alcohol | 1.0 | | | | | | | | | |
| Aerosol OT | 1.0 | | | | | | | | | |
| Arquad 2c-75% | | 3.6 | | | | | | | | |
| Nekal WS-25 | | | 7.0 | | | | | 2.7 | | |
| Tamol SN | | | 2.0 | | | | | | 1.7 | |
| Gafac RM510 | | | | 2.7 | 6.8 | 2.7 | | | 1.7 | |
| Gafac RE610 | | | | | | | | | | |
| Gafc LO529 | | | | | | | | 1.35 | | |
| Methyl Cellulose | | | | | | | | | | 3.2 |
| Aerosol GPG | | | | | | | | | | 1.6 |
| $Na_2HPO_4.7H_2O$ | | | 1.9 | | | 1.0 | 1.0 | | | 3.3 |
| NaCH (0.1 Soln.) | | | | | | 34 | | | | |
| $Na_3PO_4.12H_2O$ | | | | | | | | 1.0 | 3.4 | |
| Water | 100 | 100 | 200 | 200 | 500 | 300 | 200 | 270 | 320 | 320 |
| Epichlorohydrin | | 1 | | | | | | | | |
| Time of Reaction (hrs.) | 20: | 26 | 24* | 18* | 24* | 24* | 48 | 48 | 48 | 15* |
| Temperature | 98° | 98° | 98° | 98° | 98° | 98° | 98° | 97° | 98° | 98° |
| Yield % | 78.5 | 81.5 | 80.0 | 65 | 65 | 79 | 88 | 94.5 | 92.8 | 63 |
| Particle Size (Fischer) | — | 10-150 | 10-150 | 150-200 | — | 10 Av. | | | | |
| Particle Size (Coulter Counter) | | | | | | 16% >27μ 50% >17μ 84% >10.6μ | | 16% >15μ 50%->9.6μ 50% >15.6μ 84%->5.7μ | 84>9.7μ | 16%>24μ |

*In these examples the duration of heating was limited to a shortened period so adduction did not proceed to completion.

EXAMPLE 1

A mixture of about 114 parts (0.4 mol, 0.4 equivalent) of hexachlorocyclopentadiene, 21.6 parts (0.2 mol, 0.4 equivalent) of 1,5-cyclooctadiene, 1.4 parts of Gafac RM 510, (a commercially available anionic emulsifying agent identified as containing essentially the free acid form of complex organic phosphates), and 100 parts of water was agitated vigorously to form an aqueous emulsion. The emulsion was heated to and maintained at 98° for 26 hours under reflux conditions. The resulting mixture was cooled to ambient temperature and the emulsion was broken by the addition of acetone. The solid product was separated by filtration and the filter cake was washed with acetone. The washed product was dried. A yield of 82.5 percent of the theoretical amount of the diadduct of hexachlorocyclopentadiene and 1,5-cyclooctadiene was obtained. The product had a maximum particle size of 150-200 microns.

EXAMPLE 2

A mixture of 1410 parts (5 mols, 5 equivalents) of hexachlorocyclopentadiene, 275 parts, (2.5 mols, 5 equivalents) of 1,5-cyclooctadiene, 33.6 parts of Gafac

EXAMPLE 13

A mixture of 104 parts (1.0 mol, 1.0 equivalent) of styrene, 273 parts (1.0 mol, 1.0 equivalent) of hexachlorocyclopentadiene, 7.6 parts of Gafac RM 510 and 750 parts of water was agitated and heated under reflux conditions to 98°-100° for 13 hours. The resultant agitated emulsion was cooled to ambient temperature. Thereafter, the emulsion was broken by the addition of a small amount of methanol. The resultant solid adduct was separated by filtration and the filter cake was washed with water. The washed product was dried for 16 hours at 50° in a forced circulating air oven.

The dired product, the mono Diels-Alder adduct of styrene and hexachlorocyclopentadiene 358 parts, (95% of the theoretical amount) had a particle size of from 30 to 150 microns as measured under a microscope equipped with a calibrated scale.

EXAMPLE 14 (Comparative Experiment)

Part A

A mixture of 104 parts (1.0 mole, 1.0 equivalent) of styrene and 273 parts (1.0 mol, 1.0 equivalent) of hexachlorocyclopentadiene was heated with agitation on a steam bath to 98° substantially as described in Example 13 except that the water and the Gafac RM 510 emulsifier used in Example 13 were omitted to avoid formation of an aqueous emulsion in the reaction mass. When the temperature of the reaction mixture reached 98° exothermic production of heat from the reaction caused the reaction mixture temperature to rise above 98°. The reaction mixture was then externally cooled by water at ambient temperature so that the temperature of the mixture was not allowed to rise above 115°. After about 5 minutes from the beginning of the exothermic production of heat, the production of heat ceased. Heating of the agitated reaction mass was then continued at about 98° so that the total period of heating at the latter temperature was about 13 hours, substantially as described in Example 13 above. The reaction mixture was cooled to ambient temperature. On cooling, there was obtained as the reaction product a viscous liquid which did not crystallize on standing at ambient temperature for about five hours. A small sample of the liquid product was removed from the reaction vessel and admixed with methanol substantially as described in Experiment 1 above in an attempt to induce crystallization. When no crystallization resulted on treatment with methanol, two additional small samples of the liquid reaction product were removed and similarly treated with small amounts of ethanol and benzene, respectively, but crystallization of the liquid product did not occur. The liquid reaction mass was then allowed to stand at ambient temperature. After standing at ambient temperature for about 111 hours, the liquid reaction mixture was found to have solidified into a massive crystalline body. This crystalline product, the Diels-Alder mono-adduct of styrene and hexachlorocyclopentadiene, was in the shape of a hemisphere having a diameter of about 12 cm. and a maximum depth of about 6 cm.

Part B

In order to break up the massive crystalline body of the product adduct obtained in Part A above and thereby remove it from the reaction vessel, about 118 parts of ethanol were added to the reaction vessel and the resultant mixture was warmed on a steam bath. The resultant ethanolic slurry of the crystalline adduct was cooled to ambient temperature with agitation and filtered to recover the particulate crystalline adduct. After being dried at 41° overnight in a vacuum oven there was obtained a yield of 337 parts (89% of theory) of particulate crystalline adduct having particle sizes in the range of about 50 to 330 microns as measured under a microscope equipped with a calibrated scale.

EXAMPLE 15 (Comparative Experiment)

To a mixture of 137 parts (about 0.5 equivalents) of hexachlorocyclopentadiene 12.2 parts of Gafac RM 510 and 100 parts of water, 27 parts (about 0.5 equivalent) of cis-1,4-polybutadiene (Ameripol CB 220 of equivalent weight of about 54; number average molecular weight of about 55,000, indicating an average functionality of about 1020 olefinic double bonds per polymer molecule) were slowly added as the mixture was gradually heated to 100°. The resulting emulsion gradually became viscous as the polybutadiene was added. After the addition was completed, about 200 parts of water and 2 parts of trisodium phosphate ($Na_3PO_4 \cdot 12H_2O$) were added. The mixture was heated at its boiling temperature, under reflux conditions, for 40 hours, and was thereafter distilled with steam to remove unreacted hexachlorocyclopentadiene. After cooling the mass to ambient temperature, 105 parts of polymeric product in the form of beads were obtained by filtration of the resultant slurry. The amount of unreacted hexachlorocyclopentadiene which was recovered by steam distillation was about 40 parts by volume. The polymeric product also contained about 9.2% unreacted hexachlorocyclopentadiene as determined by ultraviolet absorption spectral analysis of the product. These results indicated that no more than about 50% of the olefinic unsaturation in the cis-polybutadiene had reacted with the hexahalocyclopentadiene.

Although the present invention has been described and illustrated with respect to certain preferred embodiments thereof, it will be obvious to those skilled in this art that modifications can be made in specific details disclosed herein without departing from the scope and spirit of the invention.

What is claimed is:

1. In a process for the preparation of a Diels-Alder adduct by carrying out the Diels-Alder reaction of a halogenated cyclopentadiene, wherein the carbon atoms of the carbon-to-carbon double bonds are perhalogenated, with a mono-olefin or diolefin capable of reacting with said halogenated cyclopentadiene to form a solid adduct, the improvement which comprises carrying out the adduction reaction with the reactants emulsified in an aqueous reaction medium employing about 0.9 to about 2.2 mole of the halogenated cyclopentadiene per mole of the olefin, the proportion of the halogenated cyclopentadiene and olefin reactants in said aqueous emulsion being about 10 to about 60 weight percent of the emulsion and the reaction temperature being about 20° Centigrade to about 160° Centigrade to obtain the solid adduct in particulate form having substantially no particles with a maximum size greater than about 200 microns.

2. The process of claim 1 in which the halogenated cyclopentadiene is a compound of the formula

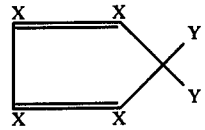

wherein X is a halogen selected from the group consisting of fluorine, chlorine, and bromine, Y is independently selected from the group consisting of fluorine, chlorine, bromine, alkyl of 1 to 10 carbon atoms, alkoxy of 1 to 10 carbon atoms, monohaloalkyl of 1 to 10 carbon atoms and monohaloalkoxy of 1 to 10 carbon atoms, wherein said halo-radicals are fluoro, chloro or bromo.

3. The process of claim 2 wherein the halogenated cyclopentadiene is adducted with a diolefin and about 1.8 to about 2.2 moles of halogenated cyclopentadiene per mole of diolefin is employed.

4. The process of claim 2 wherein the halogenated cyclopentadiene is adducted with a mono-olefin and about 0.9 to about 1.1 mole of halogenated cyclopentadiene per mole of mono-olefin is employed.

5. The process of claim 2 wherein the aqueous reaction mixture also contains a small, effective amount of an organic emulsifying agent.

6. The process of claim 5 wherein the emulsifying agent is of the anionic class of surfactants.

7. The process of claim 4 wherein the mono-olefin is styrene.

8. The process of claim 3 wherein the diolefin is 1,5-cyclooctadiene.

9. The process of claim 2 wherein the halogenated cyclopentadiene is adducted with a diolefin and about 0.9 to about 1.1 mole of halogenated cyclopentadiene per mole of diolefin is employed.

10. In a process for the preparation of a Diels-Alder adduct by reacting hexachlorocyclopentadiene and 1,5-cyclooctadiene, the improvement which comprises
   1. emulsifying the reactants in water in the proportion of about 10 to about 60 weight percent of the reactants based on the weight of the aqueous emulsion, employing about 1.8 to about 2.2 moles of hexachlorocyclopentadiene per mole of 1,5-cyclooctadiene in the presence of a small effective amount of an organic emulsifying agent,
   2. reacting the hexachlorocyclopentadiene and 1,5-cyclooctadiene at a temperature in the range of about 20° Centigrade to about 160° Centigrade to form a solid adduct in particulate form having substantially no particles with a maximum size greater than about 200 microns, and,
   3. recovering said adduct as a product of the process.

11. In the process for the preparation of a Diels-Alder adduct by carrying out the Diels-Alder reaction of a halogenated cyclopentadiene, wherein the carbon atoms of the carbon-to-carbon double bonds are perhalogenated, with a mono-olefin or diolefin capable of reacting with said cyclopentadiene to form an adduct which is a solid at least at temperatures up to about 160° Centigrade, the improvement which comprises:
   1. forming an emulsion of the reactants in water in the presence of an organic emulsifying agent wherein the emulsion comprises about 10 to about 60 weight percent of said reactants based on the total weight of the emulsion, the emulsifying agent is employed in a proportion of about 0.1 to about 10 weight percent based on the weight of said reactants, with the amount of the halogenated cyclopentadiene employed being about 0.9 to about 2.2 mole per mole of said olefin;
   2. reacting said reactants at a temperature in the range of about 20° Centigrade to about 160° Centigrade to form the solid adduct in particulate form having substantially no particles with a maximum size greater than about 200 microns, and,
   3. recovering said adduct as a product of the process.

12. The process of claim 11 wherein the product adduct is the diadduct of hexachlorocyclopentadiene and furan.

13. The process of claim 11 wherein the product adduct is the diadduct of hexachlorocyclopentadiene and cyclopentadiene.

14. The process of claim 11 wherein the product adduct is the diadduct of hexachlorocyclopentadiene and dicyclopentadiene.

15. The process of claim 11 wherein the product adduct is the diadduct of hexachlorocyclopentadiene and 1,5-cyclooctadiene.

16. The process of claim 11 wherein the product adduct is the adduct of hexachlorocyclopentadiene and cyclopentene.

* * * * *

UNITED STATES PATENT AND TRADEMARK OFFICE
CERTIFICATE OF CORRECTION

PATENT NO. : 4,053,528

DATED : October 11, 1977

INVENTOR(S) : Donald H. Thorpe

It is certified that error appears in the above-identified patent and that said Letters Patent are hereby corrected as shown below:

Column 1, line 41, "when recovered form" should read --when recovered in solid form--. Column 2, line 67, "of slid" should read --of solid--. Column 3, line 58, "1 to 1 carbon" should read --1 to 10 carbon--. Column 4, line 8, "about 1 mole" should read --about 10 mole--. Column 5, line 44, "Cyclodedecadiene" should read --Cyclododecadiene--. Column 6, line 23, "(i.e. alky of 1 to 25 carbon atoms)" should read --(i.e. alkyl of 10 to 25 carbon atoms)--. Column 9, line 37, in Table, "NaCH(0.1 Soln.)" should read --NaOH(0.1 Soln.)--. Column 9, line 41, under Ex. 3, "Time of Reaction (hrs.) 20:" should read --Time of Reaction (hrs.) 20*--. Columns 9 and 10, "84% >5.7 $\mu$ and 84 >9.7$\mu$" respectively should read --84% >5.7$\mu$ and 84% >9.7$\mu$ respectively and put under Examples 10 and 12 instead of 9 and 11. Column 10, line 59, "the dired product" should read --the dried product--.

Signed and Sealed this

Eighteenth Day of April 1978

[SEAL]

Attest:

RUTH C. MASON
Attesting Officer

LUTRELLE F. PARKER
Acting Commissioner of Patents and Trademarks